United States Patent [19]

Rivier

[11] 4,377,482
[45] Mar. 22, 1983

[54] MOBILE PHASE FOR LIQUID CHROMATOGRAPHY

[75] Inventor: Jean E. F. Rivier, La Jolla, Calif.

[73] Assignee: Salk Institute for Biological Studies, San Diego, Calif.

[21] Appl. No.: 901,117

[22] Filed: Apr. 28, 1978

[51] Int. Cl.³ ............................................. B01D 15/08
[52] U.S. Cl. ................................... 210/635; 210/656; 210/198.2; 260/112.5 R
[58] Field of Search ......................... 210/31 C; 55/67; 260/112.5 R, 112.5 H; 252/364

[56]  References Cited

U.S. PATENT DOCUMENTS 3,002,823  10/1961  Flodin et al. ..................... 210/31 C
4,042,327   8/1977  Haney ............................... 210/31 C

OTHER PUBLICATIONS

Introduction to Modern Liquid Chromatography by Snyder and Kirkland, John Wiley and Sons, New York, N.Y., pp. 219-221, 1974.

Technical Data, Gas Chromatography Bulletin 4, Fisher Scientific, Boston, Mass., dated 9/60.

*Primary Examiner*—John Adee
*Attorney, Agent, or Firm*—Fitch, Even, Tabin, Flannery & Welsh

[57]  ABSTRACT

A mobile phase for use in reversed phase high performance liquid chromatography. The mobile phase is a mixture of a polar organic solvent selected from acetonitrile and methanol and an aqueous solution of a salt of a tertiary amine and phosphoric acid or formic acid. The tertiary amines are selected from the group consisting of trialkyl amines and cyclic tertiary amines such as N-methyl morpholine, wherein the alkyl moiety is selected from methyl, ethyl, propyl, butyl and mixtures thereof.

13 Claims, No Drawings

MOBILE PHASE FOR LIQUID CHROMATOGRAPHY

The invention described herein was made in the course of work under a grant or award from the Department of Health and Human Services, formerly DHEW.

BACKGROUND OF THE INVENTION

1. Field of the Invention

The present invention relates generally to a method for resolving mixtures of chemical compounds by a chromatographic process. More particularly, the method of the present invention is directed to a particular mobile phase for use in reversed phase high performance liquid chromatography for use in resolving mixtures of chemical compounds, particularly peptides.

Chromatography is a separation method whereby individual chemical compounds which were originally present in a mixture are resolved from each other by the selective process of distribution between two phases. The distribution of chemical species to be separated occurs in a dynamic process between a mobile phase and a stationary phase. In liquid-liquid chromatography, a liquid stationary phase is held on the surface of an inert solid which serves as its support and, ideally, does not participate in the separation process. The components of a mixture having different solubilities in the stationary phase separate by migrating at different rates.

In modern liquid chromatography, the sample (a mixture of components to be separated) is introduced into a controlled stream of mobile phase at the top of the column. The effluent from the column is continuously monitored by a suitable detector, and the signals are recorded or otherwise processed. The stream of mobile phase is usually pumped under conditions of high pressure, i.e., pressure in the range of 500 to 6000 psig. Modern liquid chromatography utilizing a controlled stream of mobile phase under high pressure is usually referred to as high performance liquid chromatography (HPLC).

In liquid-liquid chromatography, the mobile phase and the stationary phase must be immiscible. Since immiscibility means automatically that the two phases must have significantly different chemical properties, only combinations of either a nonpolar mobile phase and a polar stationary phase or a polar mobile phase and a nonpolar stationary phase are feasible. Through convention, a system that uses a nonpolar stationary phase and a relatively polar mobile phase is referred to as reversed-phase chromatography. Although there is no justification to consider any stationary phase "normal," the term "reversed-phase" has persisted as a convenient general description for nonpolar stationary phases.

2. Background of the Prior Art

The mobile phase composition is an important variable in liquid-liquid chromatography. It is a particularly important variable in resolving mixtures of peptides which can have as few as two amino acids and as many as several hundred. Separation of optically different peptides, such as the dipeptide pairs L-Phe-L-Leu and L-Phe-D-Leu, are a further problem in resolving mixtures of peptides. Various mobile phase compositions are known for use in resolving peptide mixtures, such as acetonitrile in combination with a mineral salt of phosphoric acid. Such known mobile phase compositions have shown good resolution and usefulness in resolving lower molecular weight peptides, but poor resolution and recovery has been encountered when dealing with polypeptides, such as $\beta$-endorphins and proteins. A further problem encountered with use of acetonitrile and the mineral salt of phosphoric acid mobile phase compositions is that such mobile phase compositions are detrimental to the column when resolving mixtures of higher molecular weight peptides, such as human $\beta$-endorphin, ovine $\beta$-endorphin and porcine $\beta$-endorphin.

It would be desirable to provide a mobile phase composition which has high resolution and good recovery in respect to a broad range of peptides and other chemical compounds and which has high selectivity in respect to minor chemical and optical differences between closely related peptides.

SUMMARY OF THE INVENTION

It is one object of the present invention to provide a mobile phase for use in reversed-phase high performance liquid chromatography which is useful for the separation of mixtures of peptides and other chemical compounds.

It is another object of the present invention to provide a method for resolving mixtures of peptides and other chemical compounds by reversed-phase high performance liquid chromatography utilizing a mobile phase which leads to high resolution and good recovery and which is not detrimental to operation of the chromatographic column.

All the foregoing objects are achieved by utilizing a mobile phase in reversed-phase high performance liquid chromatography which comprises a mixture of a polar organic solvent selected from acetonitrile and methanol and an aqueous solution of a tertiary amine salt of phosphate or formate. The tertiary amine is selected from the group consisting of trialkyl amines, and cyclic tertiary amines such as N-alkyl morpholine, wherein the alkyl moiety is selected from the group consisting of methyl, ethyl, propyl, butyl and mixtures thereof.

The mobile phase of the present invention is useful as the eluent for reversed-phase high performance liquid chromatography. The mobile phase is useful with any of the stationary phases conventionally used in reversed-phase high pressure liquid chromatography. Such stationary phases include the pellicular column materials which were first developed for reversed-phase-high pressure liquid chromatography and the more commonly encountered siliceous microparticle column materials, with or without a "bonded" organic moiety. Nonpolar pellicular stationary phases are usually prepared from silica particles coated with a hydrocarbonaceous layer.

Preferred stationary phases are formed by bonding an organic moiety to silica gel. Silica gel is now manufactured with uniform micro-particles 5 to 10 microns in diameter. To provide silica gel with a hydrocarbonaceous bonded phase, the silica gel is usually reacted with an alkyl-trichlorosilane. As a result, the hydrocarbonaceous moiety is covalently bound to the silica surface. Most commonly, a $C_{18}$ alkyl chain is used and the octadecylsilica so obtained is the most popular stationary phase. Similar bonded phases composed of $C_2$ and $C_8$ hydrocarbonaceous moieties as well as aromatic ligands have also been introduced. A variety of hydrocarbonaceous phases are available with various particle sizes and shapes. Some bonded phases with $C_2H_4CN$ functions are also used as nonpolar stationary phases.

The mobile phase of the present invention is useful with each of the above-described stationary phases. A discussion of stationary phases is found in an article by Horvath, et al, Journal of Chromatographic Science, Vol. 15, September 1977, pp 393–404.

The mobile phase of the invention is useful in reversed-phase high performance liquid chromatography for the resolution of various chemical compounds and is particularly suitable for use with peptide mixtures. The ability of the mobile phase of the invention to resolve peptides which are closely related on the basis of size, composition and optical purity makes it ideal for use in peptide and protein analysis and peptide and protein isolation.

DETAILED DESCRIPTION OF THE INVENTION

The mobile phase of the present invention for use in reversed phase high performance liquid chromatography is a mixture of a polar organic solvent selected from acetonitrile ($CH_3CN$) and methanol and an aqueous solution of a tertiary amine salt of phosphate or formate. Suitable tertiary amines are selected from the group consisting of trialkyl amines and cyclic amines such as N-alkyl morpholine, wherein the alkyl moiety is selected from the group consisting of methyl, ethyl, propyl, butyl and mixtures thereof. Preferably, the alkyl moiety is ethyl and a preferred tertiary amine salt is triethylammonium phosphate.

The mixture contains from 0 to about 85 percent of the polar organic solvent and from about 15 to 100 percent of the tertiary amine salt solution. The solution of the tertiary amine salt is prepared by adjusting the pH of a phosphoric acid or formic acid solution with a suitable tertiary amine. The acid solution is preferably from about 0.05 to about 0.5 N with respect to phosphoric acid or formic acid and is preferably adjusted to a pH of from about 2 to about 4 with the tertiary amine. As a particular example of the tertiary amine salt solution of the invention, the pH of a 0.25 N phosphoric acid solution is brought to 3–3.5 with triethylamine. As used herein, all percentages are by volume and all temperatures are centigrade unless otherwise indicated.

As indicated, the polar organic solvent can be absent under some separation conditions. For most separations, however, a gradient of the polar organic solvent is used to ensure elution of the most nonpolar components of the starting mixture. For most separations, isocratic or gradient conditions, wherein the mobile phase comprises from about 1 to about 85 percent of the polar organic solvent and from about 15 to about 99 percent of the tertiary amine salt solution, are used. It is also preferred to use a final wash of 85 percent polar organic solvent and 15 percent tertiary amine salt solution to ensure completion of the sample recovery and to place the column in condition for the next run.

Both the phosphoric acid solution and the tertiary amine should be free of UV absorbing materials, and the solution is millipore filtered to eliminate any solid particles that might plug the column. The solution is degassed to avoid the possibility of bubble formation during decompression of the solvent before the detection system and is refrigerated prior to use to decrease the possibility of bacterial contamination.

The following examples further illustrate various features of the invention, but are intended to in no way limit the scope of the invention which is defined in the appended claims.

EXAMPLE I

A Waters Associates Model 204 Liquid Chromatograph, UK6 Injector, two 6000A Pumps and a 660 Programmer were used to evaluate the mobile phase of the present invention. A Schoeffel Model 770 Multiwave Length Detector and Linear Instruments Corp. Model 445 Chart Recorder were used as a detector and recorder. Analytical columns of the Bondapak series were used for the studies.

A triethylammonium phosphate solution was prepared by bringing the pH of 0.25 N phosphoric acid to 3–3.5 with triethylamine. A portion of the triethylammonium phosphate solution was used to prepare a second solution containing 60 percent acetonitrile. The two solutions were metered by the two pumps identified as pump A for the pure triethylammonium phosphate solution and pump B for the mixture of 40 percent triethylammonium phosphate and 60 percent acetonitrile.

The efficiency of the mobile phase for the separation of larger peptides was evaluated with a sample mixture of 5 micrograms each of LRF (MW:1181), somatostatin (MW:1636), insulin (MW:5630) and Cytochrome C (MW:12,750). A 0.4 by 30 CM Bondapak propyl nitrile No. 51928 column was used to resolve the peptide mixture. The column was operated with a back pressure of 1000 psig and a total mobile phase flow rate of 1.5 ml/min. A gradient of 12 percent to 33 percent acetonitrile was used. This corresponds to 20 percent to 55 percent of the mixed acetonitrile and triethylammonium phosphate solution of pump B. A sharp peak for LRF was noted at 8 minutes, the somatostatin peak occurred at 20 minutes, an insulin peak at 23 minutes and the Cytochrome C peak at 24 minutes. The insulin peak was recovered as pure insulin free of contaminants which were not known to be present prior to the separation set forth in the present example. Resolution and recovery were excellent, and positive identification of each peak was made by amino acid analysis. Detection of the peaks was made through UV absorbance at 210 nm. The resolution of this mixture of peptides was reproducible and no degradation of the column packing was noted after repeated runs.

EXAMPLE II

An acetonitrile/mineral salt of phosphoric acid mobile phase was used to separate human, porcine and ovine β-endorphin in accordance with the prior art. Human β-endorphin has the sequence H-Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-Tyr-Lys-Gly-Glu-OH. Ovine β-endorphin is identical to human β-endorphin with the exception of $His_{87}$ and $Gln_{91}$. Ovine β-endorphine differs from porcine β-endorphin only in the presence of one extra methyl group at position 83 which corresponds to the substitution of one Ile residue for Val. The Bondapak 0.4 by 30 CM propyl nitrile column No. 51928 was used. The back pressure was 1800 psig and the flow rate of the mobile phase was 2 ml/min. Isocratic conditions were used utilizing 32 percent $CH_3CN$ and 68 percent of 0.05 N $H_3PO_4$. The pH was adjusted to 7.50 with NaOH. The load of the β-endorphin peptides was 45 micrograms each. The separation using this prior art mobile phase was successful. The conditions used for the separation were, however, detrimental to the column which finally collapsed after about 10 runs due to slow dissolution of the support.

The mobile phase of the present invention was next used to separate the human, ovine and porcine β-endorphins described hereinabove. The same type column was used at a back pressure of 1000 psig. The flow rate of the mobile phase was 1.5 ml/min. Isocratic conditions for 14 minutes were 17.4 percent $CH_3CN$ and 82.6 percent of the triethylammonium phosphate solution of Example I. Isocratic conditions were followed by a 3-minute gradient to 24 percent $CH_3CN$ followed by isocratic conditions at 24 percent $CH_3CN$. The sample mixture contained 15 micrograms each of porcine, ovine and human β-endorphin.

A β-porcine endorphin peak was observed at 11 minutes, a β-ovine peak was observed at 14.5 minutes and a β-human endorphin peak was observed at 21 minutes. The resolution and recovery was excellent and repeated runs of the column resulted in no observable detriment to the stationary phase.

EXAMPLE III

The mobile phase of the present invention was used to resolve a tryptic digest of myelin basic protein. A Bondapak 0.4 by 30 cm $C_{18}$ No. 26332 column was used. The column was operated at a back pressure of 900 psig and a mobile phase flow rate of 1.5 ml/min. Isocratic conditions for 5 minutes were 0 percent $CH_3CN$ and 100 percent of the triethylammonium phosphate solution of Example I. This was followed by a 5-minute gradient to 18 percent $CH_3CN$, then isocratic conditions for 8 minutes at that concentration followed by a 5-minute gradient to 48 percent $CH_3CN$. The sample load was 50 micrograms of a tryptic digest of myelin basic protein. The total time for the run was less than 35 minutes.

The resolution of the various peptide fragments of the digest was excellent and the peptide fragments were isolated for further analysis.

The mobile phase of the present invention as used in reversed-phase high performance liquid chromatography is useful for resolving mixtures of various chemical compounds, particularly proteins and peptides. The use of the mobile phase of the present invention provides a means for rapid and quantitively complete recovery of pure proteins and peptides.

What is claimed is:

1. A mobile phase for use in analysis of peptides by reversed-phase high performance liquid chromatography comprising a mixture of a polar organic solvent selected from the group consisting of acetonitrile and methanol and an aqueous solution of a tertiary amine selected from the group consisting of trialkylammonium phosphate, trialkylammonium formate and N-alkyl morpholine, wherein said alkyl moiety is selected from the group consisting of methyl, ethyl, propyl, butyl and mixtures thereof.

2. A mobile phase in accordance with claim 1 wherein said polar solvent is acetonitrile and said tertiary amine salt of said solution is trialkylammonium phosphate.

3. A mobile phase in accordance with claim 2 wherein said trialkylammonium phosphate is triethylammonium phosphate.

4. A mobile phase in accordance with claim 1 wherein said phosphate or said formate moiety is present at a level of from about 0.05 to about 0.5 N and the pH of said solution is from about 2 to about 4.

5. A mobile phase in accordance with claim 4 wherein said polar solvent is acetonitrile and said tertiary amine salt of said solution is triethylammonium phosphate.

6. A method for resolving mixtures of peptides by reversed-phase high performance liquid chromatography comprising providing a column packed with hydrocarbonaceous functional groups bonded to a carrier, introducing a peptide mixture into the end of said column and eluting said column with a mobile phase comprising a mixture of a polar solvent selected from the group consisting of acetonitrile and methanol and an aqueous solution of a tertiary amine selected from the group consisting of trialkylammonium phosphate, trialkylammonium formate and N-alkyl morpholine wherein said alkyl moiety is selected from methyl, ethyl, propyl, butyl and mixtures thereof.

7. A method in accordance with claim 6 wherein said polar solvent is acetonitrile and said tertiary amine salt of said solution is trialkylammonium phosphate.

8. A method in accordance with claim 7 wherein said trialkylammonium phosphate is triethylammonium phosphate.

9. A method in accordance with claim 6 wherein said phosphate or said formate moiety is present at a level of from about 0.5 to about 0.5 N and the pH of said solution is from about 2 to about 4.

10. A method in accordance with claim 6 wherein said polar solvent is acetonitrile and said tertiary amine salt of said solution is triethylammonium phosphate.

11. A method in accordance with claim 9 wherein said acetonitrile is present at a level of from about 0 to about 85 percent, said phosphate moiety is present at a level of from about 0.1 to about 0.25 N and the pH of said solution is from about 2.5 to about 3.5.

12. A mobile phase in accordance with claim 1 wherein said polar organic solvent is present in said mixture at a level of from about 1 to about 85 percent and said tertiary amine is present in said mixture at a level of from about 15 to about 99 percent.

13. A method in accordance with claim 6 wherein said polar organic solvent is present in said mixture at a level of from about 1 to about 85 percent and said tertiary amine is present in said mixture at a level of from about 15 to about 99 percent.

* * * * *

UNITED STATES PATENT AND TRADEMARK OFFICE
CERTIFICATE OF CORRECTION

PATENT NO. : 4,377,482
DATED : March 22, 1983
INVENTOR(S) : Jean E. F. Rivier

It is certified that error appears in the above-identified patent and that said Letters Patent is hereby corrected as shown below:

On the title page,

Under references cited, add the following U.S. patent document:

3,816,386    6/1974,   Hedlund......260/112.5LH

Column 2, line 48, change "pressure" to --performance--.

Column 6, line 37, change "0.5" (first instance) to --0.05--.

Signed and Sealed this

Twelfth Day of July 1983

[SEAL]

Attest:

GERALD J. MOSSINGHOFF

Attesting Officer     Commissioner of Patents and Trademarks